United States Patent [19]

Mendicino

[11] Patent Number: 4,762,939

[45] Date of Patent: Aug. 9, 1988

[54] PROCESS FOR TRIALKOXYSILANE/TETRAALKOXYSILANE MIXTURES FROM SILICON METAL AND ALCOHOL

[75] Inventor: Frank D. Mendicino, Marietta, Ohio

[73] Assignee: Union Carbide Corporation, Danbury, Conn.

[21] Appl. No.: 102,738

[22] Filed: Sep. 30, 1987

[51] Int. Cl.$^4$ ................................................. C07F 7/04
[52] U.S. Cl. .................................................... 556/470
[58] Field of Search .......................................... 556/470

[56] References Cited

U.S. PATENT DOCUMENTS

| | | | |
|---|---|---|---|
| 2,473,260 | 6/1949 | Rochow | 260/448.8 |
| 3,072,700 | 1/1963 | de Wit | 260/448.8 |
| 3,627,807 | 12/1971 | Bleh et al. | 260/448.8 |
| 3,641,077 | 2/1972 | Rochow | 260/429 R |
| 3,775,457 | 11/1973 | Marsoka et al. | 260/448.8 A |
| 3,803,197 | 4/1974 | Anderson et al. | 260/448.8 A |
| 4,113,761 | 9/1978 | Kreuzburg et al. | 556/470 |
| 4,185,029 | 1/1980 | Kreuzburg et al. | 260/448.8 A |
| 4,211,717 | 7/1980 | Emblem et al. | 556/470 |
| 4,288,604 | 9/1981 | Magee | 556/470 |
| 4,289,889 | 9/1981 | Herdle et al. | 556/470 |
| 4,323,690 | 4/1982 | Montle et al. | 556/470 |
| 4,447,632 | 5/1984 | Mallon | 556/470 |
| 4,487,949 | 12/1984 | Mallon | 556/470 |

FOREIGN PATENT DOCUMENTS

| | | | |
|---|---|---|---|
| 107315 | 4/1978 | Japan | 556/470 U X |
| 84348 | 4/1978 | Japan | 556/470 U X |
| 146344 | 5/1978 | Japan | 556/470 U X |
| 146343 | 5/1978 | Japan | 556/470 U X |
| 163529 | 6/1979 | Japan | 556/470 U X |
| 28928 | 6/1980 | Japan | 556/470 U X |
| 28929 | 6/1980 | Japan | 556/470 U X |
| 2641 | 6/1980 | Japan | 556/470 U X |
| 16492 | 2/1981 | Japan | 556/470 U X |
| 57-099593 | 6/1982 | Japan | 556/470 |
| 61-001694A | 1/1986 | Japan | 556/470 |

*Primary Examiner*—Paul F. Shaver
*Attorney, Agent, or Firm*—Steven H. Flynn

[57] ABSTRACT

A process for producing controlled trialkoxysilane/tetraalkoxysilane mixtures by the direct reaction of silicon metal with an alcohol in the presence of a catalytically effective amount of a copper catalyst and mixed solvents, wherein at least one solvent is inert and does not degrade under the reaction conditions and at least one other solvent promotes the reaction between trialkoxysilanes and alcohol.

11 Claims, No Drawings

PROCESS FOR TRIALKOXYSILANE/TETRAALKOXYSILANE MIXTURES FROM SILICON METAL AND ALCOHOL

BACKGROUND OF THE INVENTION (a) Field of the Invention

The present invention generally relates to the production of trialkoxysilane/tetraalkyoxysilane mixtures in the catalyzed reaction between silicon metal and alcohol. In particular, the present invention relates to the use of mixed solvents to control the ratio of trialkoxysilane to tetraalkyoxysilane in the copper catalyzed reaction between silicon metal and alcohol.

(b) Prior Art

The reaction between silicon metal and alcohol is well established. As long ago as 1949, U.S. Pat. No. 2,473,260 issued to Rochow described a process for the preparation of methyl silicates from methanol and the silicon-copper masses. Similarly, U.S. Pat. No. 3,072,700 taught the preparation of silanes [(RO)$_3$SiH, (RO)$_2$SiH$_2$] from silicon metal and alcohol in a fluidized bed reactor.

Patents on the production of tetraalkylorthosilicates include U.S. Pat. No. 4,288,604 and Japanese Patent No. 1979-163529.

Patents covering the production of trialkoxysilane include U.S. Pat. No. 3,775,457. See also Japanese patents 1979-163529, 1980-28929, 1980-28929, 1980-2641, and Japanese laid-open applications 33457/1980 and 11538/1980.

Generally, in the copper catalyzed slurry reaction between silicon metal and alcohol the ratio of trialkoxysilane and tetraalkyoxysilane is not controlled. This is because the reaction of silicon metal and alcohol catalyzed by copper is exothermic and proceeds according to the following equation:

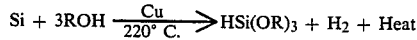

The major side reaction proceeds according to the following equation and

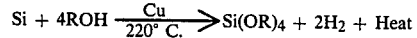

Tetraalkyoxysilane can also be formed by the secondary reaction of trialkoxysilane and alcohol catalyzed by several materials:

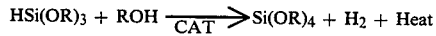

Typical materials that catalyze this secondary reaction are: copper, metal chlorides, acids, bases, and metals. Materials like HCl and FeCl$_3$ are very good catalysts. When cuprous chloride is used as the catalyst, HCl is generated early in the reaction.

Thus, a need exists to control the ratio of trialkoxysilane to tetraalkoxysilane in the copper catalyzed reaction between silicon metal and alcohol.

OBJECTS OF THE INVENTION

It is therefore an object of the invention to provide a process for producing trialkoxysilane/tetraalkyoxysilane mixtures from silicon metal and alcohol which results in a variable but controlled tetraalkyoxysilane to trialkoxysilane ratio in the product.

Another object of the invention is to provide such a process which results in a high conversion of silicon metal into trialkoxysilane/tetraalkyoxysilane product and which results in little unreacted silicon content in the reaction residue.

Other objects and advantages of the present invention will be made apparent by the description and examples which follow.

SUMMARY OF THE INVENTION

The present invention provides a process for producing trialkoxysilane/tetraalkyoxysilane mixtures of the formula HSi(OR)$_3$/Si(OR)$_4$ wherein R is an alkyl group containing from 1 to 6 carbon atoms inclusive, which process comprises:

(a) forming a reaction mixture comprising an alcohol of the formula ROH, a mixture of solvents, silicon metal, and a catalytically effective amount of a copper catalyst; and (b) reacting said alcohol with said silicon metal to produce trialkoxysilane/tetraalkyoxysilane mixtures.

The process of this invention produces product having a ratio of tetraalkyoxysilane to trialkoxysilane of from less than about 1 to 9 to greater than about 9 to 1 (on a weight basis). The process of the invention also results in high silicon conversions.

The reaction is distinguished from those employed in the past by the use of mixed solvents, at least one of which should promote the reaction between trialkoxysilane and alcohol to produce tetraalkyoxysilanes.

DETAILED DESCRIPTION OF THE INVENTION

In accordance with the present invention, the ratio of tetraalkyoxysilanes to trialkoxysilanes produced from the copper catalyzed reaction between silicon metal and alcohol is controlled by the use of mixed solvents.

Silicon

The silicon metal reactant used in the process of this invention can generally be any commercially available grade of silicon in particulate form. A typical composition of commercial silicon metal useful in this invention, expressed in percent by weight, is Silicon-98.5%; Iron-less than 0.50%; Aluminum-0.20 to 0.35%; Calcium-0.02 to 0.10%; Water-less than 0.1%; Lead-less than 10 ppm; Boron-less than 20 ppm. Generally smaller particle size (less than about 50 mesh) is preferred for ease of processing. Sieving of ground silicon to regulate particle size is optional.

The presence of tin in the reaction has adverse effects on the reaction rate and/or the selectivity for tetraalkyoxysilane and so should be avoided (e.g. amounts as low as 75 parts per million shown an adverse effect on the reaction).

Alcohol

The alcohols which are useful in the process of this invention are those in the formula ROH wherein R is an alkyl group containing from 1 to 6 carbon atoms, inclusive. Preferably R is an alkyl group containing from 1 to 3 carbon atoms inclusive. The most preferred alcohols are methanol and ethanol.

Catalyst

The copper catalyst used in the process of this invention is present in an amount effective to catalyze the reaction. Generally an effective amount ranges from about 0.01 to about 5 parts by weight of catalyst per 100 parts by weight of the silicon metal. Usually the amount of copper will be from about 0.1 to about 2.6 parts by weight per 100 parts by weight of the silicon metal. The preferred amount of copper is from about 0.1 to about 0.7 parts by weight per 100 parts by weight of silicon metal.

The preferred catalysts employed in the process of the instant invention are powdered metallic copper, any anhydrous copper compound, or mixtures thereof. Metallic silver, its compounds and their mixtures are also known to be effective catalysts.

Examples of copper compounds suitable for use individually or in mixtures are the copper oxides, e.g. cupric oxide and cuprous oxide; copper halides, e.g. cupric chloride, cuprous chloride, cuprous bromide, cupric bromide; copper nitrides, copper salts of lower aliphatic acids such as cupric formate and cupric acetate; copper carbonates; copper hydroxides; copper cyanides; intermetallic copper compounds such as lead-free bronzes and brasses, and copper acetylacetonate. This, however, is not a restrictive or exclusive list.

Copper compounds specifically to be avoided are those such as copper phosphide, copper sulfides and inter-metallic compounds of lead and copper.

Preferably, stabilized copper (II) hydroxide is employed.

Solvents

The solvents useful in the process of this invention are a mixture of a first, inert solvent that does not degrade under the reaction conditions and a second solvent that promotes the reaction between trialkoxysilane and alcohol to produce tetraalkyoxysilane.

The first, inert solvent is a high temperature stable organic solvent such as THERMINOL ® and dodecylbenzene. THERMINOL ® is the Monsanto Company trade name for heat transfer fluids.

The second solvent is a Lewis base that promotes the reaction between trialkoxysilanes and alcohol. Preferably a Lewis base with a pKa greater than 7. For example, the second solvent can be a tertiary amines such as a Kemamine ® or polyethers such as methoxytriglycol (MTG) or aromatic ethers such as diphenyl oxide.

The amount of solvent employed is a function of the amount of silicon present. Generally, from 2 parts of silicon per one part of mixed solvent (2:1) to 1 part of silicon per four parts of mixed solvent (1:4) will be required. Preferably this ratio will range from 1:1 to 1:2. Within the mixed solvent itself, the greater the amount of the second solvent the higher the amount of tetraalkoxysilane recovered.

Reaction Conditions

The silicon metal, catalyst and solvent can be added together in any order. Generally, the reaction is run in a slurry and the alcohol is fed into the slurry as a gas or liquid at a fixed rate. The reaction typically displays a one or two hour induction period. The initial alcohol feed rate is therefore low and is brought up as the reaction progresses. Generally, once the reaction is running, the alcohol feed rate can be adjusted to give the desired level of alcohol conversion. One skilled in the art can readily adjust the feed rate in a given reaction run by monitoring the product composition. If the feed rate is too high the product stream will contain a larger proportion of unreacted alcohol.

The reaction is generally conducted at temperatures above about 150° C. but below such a temperature as would degrade or decompose the reactants or solvents. Preferably the reaction temperature is maintained in a range from about 200° C. to about 240° C. The reaction could of course be run at higher temperatures although at no particular advantage.

The pressure at which the reaction is conducted is not critical and can be varied from subatmospheric to superatmospheric. The reaction is generally run at about atmospheric pressure.

Preferably the contents of the reaction mixture are agitated to maintain a well mixed slurry of the silicon particles and alcohol in the solvent. The reaction mixture need not be insulated since refluxing would encourage further reaction of the trialkoxysilane with the alcohol, resulting in the formation of tetraalkoxysilane.

Whereas, the exact scope of the instant invention is set forth in the appended claims, the following specific examples illustrate certain aspects of the present invention and, more particularly, point out methods of evaluating the same. However, the examples are set forth for illustration only and are not to be construed as limitations on the present invention except as set forth in the appended claims. All parts and percentages are by weight unless otherwise specified.

EXAMPLES

The reactions were run in a 1000 milliliter four neck flask charged with 50 grams of silicon metal, solvents, and catalyst. Alcohol was added either via a gravity feed constant addition funnel or through an FMI ® pump and flow was controlled using a micrometer adjustment. The reaction temperature was controlled using a thermometer and an I²R ® Thermo-O-Watch. The reactants were agitated using a mechanical stirrer, i.e., an air motor, with a teflon blade and glass shaft. A short (about 12") Vigreux column was used to stop entrainment of the solvent. Product examples were removed at time intervals through a distillation head with a nitrogen blow-by and collected in a 250 milliliter receiver. The product cuts or samples were taken on a 0.5–2 hour basis and 2 to 5 gram samples were submitted in pressure bottles for gas chromatographic analysis. The reaction was run at 220° C. until no more silicon metal was converted to volatile products.

COMPARATIVE EXAMPLES A–D

Several standard experiments were run in which the choice of solvent was the only variable. In each experiment, 50 grams of silicon metal, 1.3 grams of cuprous chloride and solvent were charged to the pot and heated to 220° C., then methanol was added continuously (about 30–50 grams/hour) while the product was removed continuously. The solvents that were used are:

| Solvent | Experiment No. |
| --- | --- |
| Diphenyl Oxide | A |
| THERMINOL ® 60 | B |
| Dodecylbenzene | C |
| THERMINOL ® 66 | D |

COMPARATIVE EXAMPLE E

A sodium catalyzed reaction was run using methoxytriglycol (MTG) as the solvent. At 225° C., with a continuous methanol feed, the reaction between the silicon metal and methanol occurred to produce predominantly tetramethoxysilane with very low levels of trimethoxysilane. After 25.9 hours of reaction, the experiment was terminated at 69 wt. % silicon conversion. See Table 5 for details which show that this solvent does not provide good control over the ratio of trimethoxysilane/tetramethoxysilane (TRI/TETR).

EXAMPLES 1-6

Experiment examples 1 through 4 were consistent in that, 5.0 grams of copper catalyst was used in each, the alcohol feed was maintained at about 30-50 grams per hour and the mean temperature of reaction was at 239° C. The type of solvents, solvent ratios and silicon charge were purposely varied to indicate the possibilities of the given reaction.

EXAMPLE 1 (Table 6)

This reaction was run using a 50:50 mixture of THERMINOL ® and KEMAMINE ® as the mixed solvents. Copper chloride (5.0 grams) was used as the catalyst and a total charge of 75.0 grams silicon was added. The alcohol was fed (for 47 hours) to the reaction, which had a mean temperature of 226° C. The product of this reaction was predominantly tetramethoxysilane with a silicon conversion of about 90%.

EXAMPLE 2 (Table 7)

The second reaction used a 50:50 mixture of THERMINOL ® and methoxytriglycol (MTG) as the mixed solvents. The 5.0 grams of cuprous chloride catalyst level was consistent with Example 1. The mean temperature of the reaction was 238° C. and two 50.0 gram silicon charges were made. The first 50.0 gram charge gave 75% silicon conversion but the second silicon charge had a much lower conversion. This reaction, lasting 31.5 hours, gave a good ratio of tetramethoxysilane to trimethoxysilane, varying from about 3 or 4 to 1.

EXAMPLE 3 (Table 8)

The mixed solvents in this reaction were 75% THERMINOL ® and 25% KEMAMINE ®. The catalyst charge was a consistent 5.0 grams of cuprous chloride. The mean temperature was 243° C. only slightly elevated over previous reactions. Only one initial silicon charge of 50.0 grams was made and the silicon conversion was 62%. The yield of tetramethoxysilane was predominant during the 23 hours of the reaction.

EXAMPLE 4 (Table 9)

In this reaction the mixed solvents are THERMINOL ® and KEMAMINE ® with KEMAMINE ® amounting to only 5% of the 200 gram solvent charge. The catalyst was cuprous chloride in the amount of 5.0 grams. The silicon conversion was only 67% but the reaction covered only 11.3 hours. The mean temperature of this reaction was 252° C. and yield of the tetramethoxysilane and trimethoxysilane mix was typically high on the side of tetramethoxysilane but more trimethoxysilane was produced than in previous reactions. This reaction as compared to previous reactions shows that by varying the components of the mixed solvents, the yield of the resulting products can also be varied.

EXAMPLE 5 (Table 10)

Example 5 used only 2.0% KEMAMINE ® to 98% THERMINOL ® as the mixed solvent of 100.00 grams. Cu(II)OH (0.66 wt-%) was used as the catalyst level, a somewhat lower level of copper than previous examples. The temperature of the reaction was kept at 220° C.±3° C., the temperature control is more precise at this time. The alcohol feed is more precisely controlled at 39-42 grams per hour. As the KEMAMINE ® level is dropped the ratio of trimethoxysilane to tetramethoxysilane has increased. The total product yield was good at 85%.

EXAMPLE 6 (Table 11)

To demonstrate a greater exhibition of control of reactivity and catalyst function; this reaction was run with the usual 50.0 gram charge of silicon and 2% KEMAMINE ® and 98% THERMINOL ®. No catalyst was added for 15.5 hours while the reaction was at a temperature of 220° C. and the alcohol at a constant feed, after this time period, catalyst (stabilized copper II hydroxide) 0.66% was added. The reaction then produced about equal quantities of tetramethoxysilane and trimethoxysilane even though the silicon conversion was only 72%.

TABLE 1

Comparative Example A
Charge: Si - 50.0 grams Si Metal 65 × 150 (PHP)
Catalyst - 5 grams Cuprous Chloride
Solvent - 200 cc/Diphenyl Oxide (Dow #810313)

| | | | | | | |
|---|---|---|---|---|---|---|
| Sample Collected, Grams | 21.2 | 9.0 | 10.0 | 12.0 | 26.5 | — |
| Reaction Time, Minutes | 120 | 94 | 108 | 165 | 120 | — |
| MeOH Feed, Grams | 22.2 | 9.5 | 11.1 | 11.9 | 27.7 | 7.1 |
| GCA | | | | | | |
| MeOH | 24.2 | 60.7 | 70.5 | 77.7 | 36.8 | 64.4 |
| HSi(OMe)$_3$ | 16.1 | 5.5 | 10.7 | 7.4 | 38.0 | 19.5 |
| Si(MeO)$_4$ | 54.8 | 28.5 | 12.5 | 10.3 | 13.0 | 5.9 |
| Others (Si) | 2.7 | 4.7 | 3.8 | 1.0 | 2.3 | 1.9 |
| Solvent | 3.2 | 0.6 | 2.4 | 3.6 | 9.9 | 8.3 |
| Si Conversion | 50.0 | 46.51 | 45.83 | 45.27 | 44.81 | 41.73 |
| (Si in Pot Grams) | | | | | | |
| Total Si in Sample | 3.487 | 0.683 | 0.563 | 0.459 | 3.086 | — |
| gms/hour | 1.744 | 0.436 | 0.313 | 0.167 | 1.542 | — |
| wt %/hour | 3.49 | 0.94 | 0.68 | 0.37 | 3.44 | — |
| MeOH Conversion | | | | | | |
| Feed Rate gms/hour | 11.1 | 6.06 | 6.17 | 4.33 | 13.85 | — |
| Wt %/hour | | | | | | |
| Reaction Condition | | | | | | |
| Temperature, °C. | 220* | 250 | 250** | 250** | 250* | 250* |
| HSi(OMe)$_3$/Si(MeO)$_4$ Ratio | 0.29 | 0.19 | 0.86 | 0.72 | 2.92 | 3.31 |

*Sample on reflux.
**Added NH$_4$Cl to reactivate system

TABLE 2

Comparative Example B
Charge: Si - 50.0 grams Active Mass (PHP)
Catalyst - 5 grams Cuprous Chloride
Solvent - 200 grams THERMINOL ® 60

| | | | | | | | | | | | | |
|---|---|---|---|---|---|---|---|---|---|---|---|---|
| Sample Collected, Grams | 19.9 | 70.6 | 75.9 | 69.6 | 34.2 | 26.4 | 10.0 | 16.6 | 16.3 | 11.7 | 75.2 | 79.8 | 71.3 |

TABLE 2-continued

Comparative Example B
Charge: Si - 50.0 grams Active Mass (PHP)
Catalyst - 5 grams Cuprous Chloride
Solvent - 200 grams THERMINOL ® 60

| | | | | | | | | | | | | | |
|---|---|---|---|---|---|---|---|---|---|---|---|---|---|
| Reaction Time, Minutes | 100 | 80 | 75 | 60 | 120 | 120 | 120 | 120 | 120 | 120 | 60 | 120 | 120 |
| MeOH Feed, Grams | 20.6 | 58.5 | 58.5 | 72.0 | 30.8 | 25.3 | 11.1 | 15.8 | 17.4 | 12.7 | 57.8 | 68.1 | 61.7 |
| GCA | | | | | | | | | | | | | |
| MeOH | 34.9 | 56.6 | 62.9 | 65.7 | 52.6 | 50.2 | 34.7 | 41.6 | 44.2 | 39.4 | 65.2 | 62.6 | 66.6 |
| HSi(OMe)$_3$ | 9.9 | 20.5 | 19.4 | 17.9 | 34.5 | 39.9 | 55.3 | 47.5 | 48.4 | 52.7 | 16.8 | 23.0 | 17.0 |
| Si(MeO)$_4$ | 44.4 | 8.6 | 2.7 | 1.4 | 4.2 | 4.3 | 5.8 | 6.8 | 4.6 | 4.4 | 2.1 | 3.5 | 6.7 |
| Others* (Si) | 4.8 | 3.2 | 2.5 | 2.2 | 3.5 | 2.3 | 3.3 | 3.3 | 2.7 | 3.3 | 2.3 | 1.9 | 1.5 |
| Solvent | 6.0 | 11.1 | 12.5 | 12.8 | 5.3 | 3.3 | 0.9 | 0.8 | 0.04 | 0.2 | 13.6 | 9.0 | 7.5 |
| Si Conversion (Si in Pot grams) | 50.0 | 47.7 | 42.7 | 38.5 | 35.1 | 31.9 | 29.1 | 27.6 | 25.46 | 23.4 | 21.8 | 18.2 | 13.1 |
| Total Si in Sample | 2.299 | 4.96 | 4.193 | 3.391 | 3.248 | 2.766 | 1.452 | 2.144 | 2.050 | 1.599 | 3.588 | 5.075 | 4.022 |
| gms/hour | 1.38 | 3.72 | 3.35 | 3.39 | 1.62 | 1.38 | 0.726 | 1.07 | 1.02 | 0.799 | 3.59 | 2.54 | 2.01 |
| wt %/hour | 2.75 | 7.80 | 7.86 | 8.81 | 4.63 | 4.34 | 2.49 | 3.88 | 4.03 | 3.42 | 16.5 | 13.9 | 15.4 |
| MeOH Conversion | | | | | | | | | | | | | |
| Feed Rate gms/hour | 12.4 | 43.9 | 46.8 | 7.2 | 15.4 | 12.7 | 5.6 | 7.9 | 8.7 | 6.35 | 57.8 | 34.0 | 30.9 |
| Wt %/hour | | | | | | | | | | | | | |
| Reaction Condition | | | | | | | | | | | | | |
| Temperature, °C. | 254 | 255 | 250 | 252 | 259 | 256 | 255 | 258 | 261 | 262 | 257 | 261 | 260 |
| HSi(OMe)$_3$/Si(MeO)$_4$ Ratio | 0.22 | 2.38 | 7.19 | 12.79 | 8.21 | 9.28 | 9.53 | 6.99 | 10.52 | 11.98 | 8.00 | 6.57 | 2.77 |
| Sample Collected, Grams | 46.5 | 22.3 | 18.8 | 6.78 | 63.2 | 68.1 | 54.9 | 37.8 | 57.5 | 76.9 | 37.8 | 64.0 | 62.5 | 71.4 |
| Reaction Time, Minutes | 105 | 120 | 120 | 60 | 120 | 150 | 150 | 120 | 120 | 120 | 75 | 120 | 120 | 120 |
| MeOH Feed, Grams | 44.3 | 23.7 | 19.0 | 7.91 | 59.4 | 63.3 | 52.2 | 35.6 | 51.4 | 70.4 | 36.4 | 55.4 | 57.8 | 64.9 |
| GCA | | | | | | | | | | | | | | |
| MeOH | 87.6 | 97.0 | 98.1 | 98.2 | 58.7 | 48.8 | 49.1 | 59.5 | 55.5 | 61.3 | 56.5 | 45.6 | 81.7 | 90.8 |
| HSi(OMe)$_3$ | 0.9 | — | — | — | 25.3 | 39.2 | 40.7 | 29.8 | 27.2 | 24.8 | 31.6 | 36.0 | 3.7 | — |
| Si(MeO)$_4$ | 6.3 | 1.2 | 0.6 | 0.2 | 8.9 | 6.6 | 6.9 | 7.6 | 10.2 | 4.8 | 6.4 | 11.9 | 8.1 | 0.6 |
| Others* (Si) | 0.9 | 0.2 | 0.1 | 0.1 | 1.5 | 1.3 | 1.1 | 1.4 | 1.8 | 2.2 | 1.8 | 1.9 | 1.3 | 1.0 |
| Solvent | 4.3 | 1.6 | 1.2 | 1.6 | 5.6 | 4.0 | 2.2 | 1.7 | 5.3 | 6.9 | 3.7 | 4.6 | 5.2 | 7.6 |
| Si Conversion (Si in Pot grams) | 9.10 | 8.37 | 8.31 | 8.28 + 25.0 | 33.28 | 28.4 | 21.2 | 15.2 | 39.96 | 32.05 | 26.6 | 23.26 | 16.3 | 14.0 |
| Total Si in Sample | 0.732 | 0.060 | 0.025 | 0.0041 | 4.924 | 7.158 | 5.965 | 3.236 | 4.908 | 5.446 | 3.343 | 6.970 | 1.650 | 0 |
| gms/hour | 0.418 | 0.030 | 0.013 | 0.004 | 2.46 | 2.86 | 2.39 | 1.62 | 2.45 | 2.72 | 2.67 | 3.49 | 0.83 | 0 |
| wt %/hour | 4.60 | 0.36 | 0.16 | 0.050 | 7.40 | 10.08 | 11.25 | 10.64 | 6.64 | 8.50 | 10.06 | 15.00 | 5.06 | 0 |
| MeOH Conversion | | | | | | | | | | | | | | |
| Feed Rate gms/hour | 25.5 | 11.9 | 9.5 | 7.9 | 29.7 | 25.3 | 20.9 | 17.8 | 25.7 | 35.2 | 29.1 | 27.7 | 28.9 | 3 |
| Wt %/hour | | | | | | | | | | | | | | |
| Reaction Condition | | | | | | | | | | | | | | |
| Temperature, °C. | 258 | 255 | 250 | 149** | 208 | 231 | 215 | 245 | 241 | 252 | 243 | 240 | 218 | |
| HSi(OMe)$_3$/Si(MeO)$_4$ Ratio | 0.14 | — | — | — | 2.84 | 5.94 | 5.90 | 3.92 | 2.67 | 5.17 | 4.94 | 3.03 | 0.46 | |

*Includes Heavies
**Reflux take-off

TABLE 3

Comparative Example C
Charge - Si - 50.0 grams Si Metal (65 × 150)
Catalyst - 1.30 grams Cuprous Chloride
Solvent - 100 ml, 85.7 grams Dodecylbenzene

| | | | | | | | | | | | |
|---|---|---|---|---|---|---|---|---|---|---|---|
| Sample Collected, Grams | 41.9 | 55.7 | 58.7 | 48.2 | 50.5 | 32.1 | 53.1 | 36.7 | 39.7 | 32.1 | 21.1 |
| Reaction Time, Minutes | 69 | 100 | 53 | 71 | 60 | 61 | 73 | 88 | 118 | 119 | 69 |
| MeOH Feed, Grams | 44.3 | 54.6 | 57.0 | 52.2 | 46.7 | 33.2 | 51.4 | 37.2 | 37.2 | 34.8 | 21.4 |
| GCA | | | | | | | | | | | |
| MeOH | 40.4 | 42.6 | 52.6 | 46.4 | 50.0 | 47.7 | 53.0 | 54.0 | 82.5 | 93.1 | 95.4 |
| HSi(OMe)$_3$ | 53.8 | 49.1 | 41.2 | 46.4 | 42.9 | 46.4 | 38.6 | 39.8 | 11.2 | 0.5 | 0.05 |
| Si(MeO)$_4$ | 4.8 | 7.6 | 9.3 | 6.6 | 6.7 | 0.6 | 8.0 | 5.8 | 6.2 | 6.2 | 4.5 |
| Others (Si) | 0.6 | 0.4 | 0.5 | 0.3 | 0.3 | 0.1 | 0.3 | 0.2 | 0.1 | 0.3 | 0.02 |
| Solvent and Heavies | 0.5 | 0.9 | 0.3 | 0.3 | 0.1 | 0.04 | 0.1 | 0.2 | — | 0.1 | 0.04 |
| Si Conversion (Si in Pot grams) | 50.0 | 44.4 | 37.3 | 31.1 | 25.3 | 19.7 | 15.9 | 10.4 | 6.64 | 5.16 | 4.73 |
| Total Si in Sample | | 5.602 | 7.108 | 6.191 | 5.752 | 5.630 | 3.757 | 5.523 | 3.761 | 1.483 | 0.43 | 0.178 |
| gms/hour | | 4.87 | 4.26 | 7.04 | 4.87 | 5.63 | 3.68 | 4.53 | 2.56 | 0.75 | 0.21 | 0.16 |
| wt %/hour | | 9.74 | 9.59 | 18.9 | 15.7 | 22.3 | 18.7 | 28.5 | 24.6 | 11.3 | 4.17 | 3.28 |
| MeOH Conversion | | | | | | | | | | | |
| Feed Rate gms/hour | 38.5 | 32.8 | 64.8 | 44.2 | 46.7 | 32.5 | 42.1 | 25.3 | 18.9 | 17.6 | 18.6 |
| Reaction Condition | | | | | | | | | | | |
| Temperature, °C. | 220 | — | — | — | — | — | — | — | — | — | — |
| HSi(OMe)$_3$/Si(MeO)$_4$ Ratio | 11.2 | 6.4 | 7.8 | 7.0 | 6.4 | 8.3 | 4.8 | 6.9 | 1.8 | 0.08 | 0.01 |

TABLE 4

Comparative Example D
Charge - Si - 50.0 grams 65 × 150 Si Metal
Catalyst - 1.30 grams Cuprous Chloride
Solvent - 100 cc THERMINOL ® 66

| | | | | | | | | | | |
|---|---|---|---|---|---|---|---|---|---|---|
| Sample Collected, Grams | 74.3 | 85.1 | 91.9 | 78.2 | 77.4 | 81.9 | 57.5 | 78.3 | 80.7 | 77.6 |
| Reaction Time, Minutes | 120 | 120 | 135 | 120 | 120 | 120 | 90 | 120 | 120 | 120 |
| MeOH Feed, Grams | 78.3 | 79.1 | 87.8 | 76.8 | 76.8 | 79.9 | 55.4 | 77.6 | 81.5 | 78.3 |
| GCA | | | | | | | | | | |
| MeOH | 53.7 | 47.6 | 47.0 | 57.2 | 65.8 | 77.3 | 84.2 | 96.8 | 99.4 | 99.7 |
| HSi(OMe)$_3$ | 30.6 | 44.4 | 46.8 | 36.4 | 24.4 | 10.7 | 0.9 | 0.2 | 0.1 | — |
| Si(MeO)$_4$ | 14.5 | 7.4 | 5.7 | 5.9 | 9.4 | 11.8 | 14.6 | 2.7 | 0.3 | 0.2 |
| Others (Si) | 1.1 | 0.6 | 0.5 | 0.5 | 0.4 | 0.2 | 0.3 | 0.2 | 0.1 | — |
| Solvent and Heavies | 0.09 | 0 | 0 | 0 | 0 | 0 | 0 | 0.1 | 0.1 | 0.1 |
| Si Conversion (Si in Pot grams) | 50.0 | 42.6 | 32.65 | 21.7 | 14.2 | 8.45 | 4.62 | 2.92 | 2.46 | 2.38 |
| Total Si in Sample | 7.39 | 9.95 | 10.94 | 7.47 | 5.75 | 3.83 | 1.70 | 0.46 | 0.082 | 0.029 |
| gms/hour | 3.70 | 4.97 | 4.86 | 3.74 | 2.87 | 1.91 | 1.14 | 0.23 | 0.041 | 0.014 |
| wt %/hour | 7.39 | 11.7 | 14.9 | 17.2 | 20.2 | 22.7 | 24.6 | 7.90 | 1.66 | 0.60 |
| MeOH Conversion | | | | | | | | | | |
| Feed Rate gms/hour | 39.2 | 39.6 | 39.0 | 38.4 | 38.4 | 40.0 | 36.9 | 38.8 | 40.8 | 39.2 |
| Reaction Condition | | | | | | | | | | |
| Temperature, °C. | 220 | 221 | 220 | 220 | 220 | 221 | 220 | 220 | 220 | 220 |
| HSi(OMe)$_3$/Si(MeO)$_4$ Ratio | 2.11 | 6.0 | 8.21 | 6.17 | 2.60 | 0.91 | 0.062 | 0.074 | 0.33 | — |

TABLE 5

Comparative Example E
Charge: - Si - 50.0 grams Si Metal 65 × 150
Catalyst - 42.0 grams Sodium Methylate
Solvent - 207.9 grams MTG

| | | | | | | | | | | | | | |
|---|---|---|---|---|---|---|---|---|---|---|---|---|---|
| Sample Collected, Grams | 25.5 | 18.3 | 18.8 | 9.2 | 22.3 | 38.2 | 48.0 | 56.4 | 49.0 | 50.8 | 51.3 | 48.0 | 47.8 |
| Reaction Time, Minutes | 27 | 41 | 257 | 72 | 38 | 117 | 112 | 76 | 181 | 152 | 131 | 177 | 65 |
| MeOH Feed, Grams | None | 19.8 | 26.1 | 2.4 | 44.3 | 32.4 | 40.0 | 41.1 | 47.48 | 31.66 | 44.3 | 43.5 | 37.2 |
| GCA | | | | | | | | | | | | | |
| MeOH | 99.94 | 99.89 | 99.66 | — | 60.38 | 33.06 | 40.57 | 61.28 | 50.35 | 57.07 | 62.37 | 61.68 | 70.96 |
| HSi(OMe)$_3$ | 0.03 | 0.05 | 0.12 | — | 2.23 | 0.35 | 0.18 | 0.34 | 0.11 | 0.07 | 0.148 | 0.10 | 0.11 |
| Si(MeO)$_4$ | — | 0.03 | 0.13 | — | 13.77 | 55.19 | 50.43 | 32.36 | 41.80 | 35.30 | 33.09 | 32.24 | 23.19 |
| Others | — | — | — | — | 9.68 | 2.21 | 1.20 | 0.82 | 1.34 | 1.18 | 0.83 | 1.10 | 1.12 |
| Solvent | 0.03 | 0.02 | 0.10 | — | 12.47 | 9.19 | 7.57 | 5.21 | 6.41 | 6.38 | 3.57 | 4.88 | 4.62 |
| Si Conversion (Si in Pot grams) | 50.00 | 50.00 | 50.00 | — | 49.99 | 48.81 | 44.70 | 40.09 | 36.58 | 32.64 | 29.19 | 25.95 | 22.97 |
| Total Si in Sample | 0.002 | 0.003 | 0.010 | — | 1.18 | 4.11 | 4.61 | 3.51 | 3.94 | 3.45 | 3.24 | 2.98 | 2.18 |
| gms/hour | 0.004 | 0.005 | 0.002 | — | 1.86 | 2.11 | 2.47 | 2.77 | 1.30 | 1.36 | 1.48 | 1.01 | 2.01 |
| wt %/hour | 0.008 | 0.009 | 0.005 | — | 3.72 | 4.32 | 5.53 | 6.92 | 3.57 | 4.17 | 5.09 | 3.90 | 8.75 |
| MeOH Conversion | | | | | | | | | | | | | |
| Feed Rate gms/hour | 0 | 29.0 | 6.23 | — | 69.9 | 16.6 | 21.4 | 32.4 | 15.7 | 12.5 | 20.3 | 14.7 | 34.3 |
| W %/Hour | — | — | — | — | — | — | — | — | — | — | — | — | — |
| Reaction Condition | | | | | | | | | | | | | |
| Temperature, °C. | 150 | 150 | 150 | 260 | 225 | 225 | 225 | 225 | 225 | 225 | — | — | — |
| HSi(OMe)$_3$.Si(MeO)$_4$ Ratio | — | — | — | — | 0.16 | 0.006 | 0.004 | 0.011 | 0.003 | 0.002 | 0.004 | 0.003 | 0.005 |

| | | | | | | | |
|---|---|---|---|---|---|---|---|
| Sample Collected, Grams | 40.3 | 44.9 | 46.2 | 49.7 | 46.3 | 48.5 | 35.8 |
| Reaction Time, Minutes | 85 | 72 | 84 | 58 | 42 | 87 | 75 |
| MeOH Feed, Grams | 34.0 | 38.0 | 36.4 | 47.48 | 39.57 | 41.94 | 30.01 |
| GCA | | | | | | | |
| MeOH | 78.27 | 87.77 | 83.84 | 83.15 | 84.30 | 83.96 | 83.94 |
| HSi(OMe)$_3$ | 0.13 | 0.19 | 0.10 | 0.06 | — | 0.05 | 0.04 |
| Si(MeO)$_4$ | 17.14 | 3.80 | 6.85 | 9.02 | 8.55 | 8.72 | 9.13 |
| Others | 0.96 | 1.59 | 1.44 | 1.09 | 0.98 | 0.78 | 0.74 |
| Solvent | 3.51 | 6.58 | 7.78 | 6.69 | 6.18 | 6.50 | 6.15 |
| Si Conversion (Si in Pot grams) | 20.79 | 19.42 | 18.92 | 18.17 | 17.21 | 16.38 | 15.51 |
| Total Si in Sample | 1.37 | 0.50 | 0.75 | 0.96 | 0.83 | 0.87 | 0.67 |
| gms/hour | 0.97 | 0.42 | 0.53 | 1.03 | 1.19 | 0.60 | 0.53 |
| wt %/hour | 4.66 | 2.14 | 2.82 | 5.64 | 6.92 | 3.67 | 3.44 |
| MeOH Conversion | | | | | | | |
| Feed Rate gms/hour | 24.0 | 31.7 | 26.0 | 49.1 | 56.5 | 28.9 | 24.0 |
| W %/Hour | — | — | — | — | — | — | — |
| Reaction Condition | | | | | | | |
| Temperature, °C. | — | — | — | — | — | — | — |
| HSi(OMe)$_3$.Si(MeO)$_4$ Ratio | 0.008 | 0.050 | 0.015 | 0.007 | 0.006 | 0.006 | 0.004 |

*Sample discarded and not analyzed - taken off to reach higher reaction temperature.

TABLE 6

Charge - Si - 50.0 grams Active Mass (PHP)
Catalyst - 5 grams Cuprous Chloride
Solvent - 101 grams THERMINOL ®

TABLE 6-continued 101 grams KEMAMINE ® (50%)

| | | | | | | | | | | | |
|---|---|---|---|---|---|---|---|---|---|---|---|
| Sample Collected, Grams | 43.5 | 19.7 | 6.82 | 36.3 | * | 44.0 | 41.0 | 25.5 | 38.9 | 63.3 | * |
| Reaction Time, Minutes | 90 | 120 | 60 | 120 | * | 120 | 120 | 60 | 150 | 150 | * |
| MeOH Feed, Grams | 38.0 | 19.8 | 7.12 | 40.4 | * | 35.6 | 38.8 | 21.4 | 35.6 | 61.7 | * |
| GCA | | | | | | | | | | | |
| MeOH | 16.1 | 1.4 | 0.021 | 13.8 | — | 5.2 | 7.1 | 4.3 | 38.9 | 83.3 | 92.1 |
| HSi(OMe)$_3$ | 0.04 | — | 10.8 | 0.10 | 32.5 | 0.036 | — | — | — | — | — |
| Si(MeO)$_4$ | 67.6 | 87.9 | 80.9 | 76.5 | 60.9 | 85.6 | 86.7 | 87.4 | 53.9 | 14.0 | 5.9 |
| Others (Si) | 3.0 | 5.2 | 3.4 | 2.4 | 2.4 | 1.6 | 0.5 | 0.2 | 0.3 | 0.1 | 0.04 |
| Solvent | 13.3 | 5.5 | 4.9 | 7.2 | 4.2 | 7.6 | 5.6 | 8.1 | 6.8 | 2.6 | 2.0 |
| Si Conversion | 50.0 | 44.3 | 40.9 | 39.7 | — | 34.4 | 27.3 | 20.7 | 16.6 | 12.7 | — |
| (Si in Pot grams) | | | | | | | | | | | |
| Total Si in Sample | 5.271 | 3.425 | 1.239 | 5.234 | — | 7.103 | 6.595 | 4.117 | 3.889 | 1.647 | — |
| gms/hour | 3.81 | 1.71 | 1.24 | 2.66 | — | 3.55 | 3.30 | 4.12 | 1.56 | 0.66 | — |
| wt %/hour | 7.63 | 3.87 | 3.03 | 6.71 | — | 10.3 | 12.1 | 19.9 | 9.37 | 5.19 | — |
| MeOH Conversion | | | | | | | | | | | |
| Feed Rate gms/hour | 25.3 | 9.9 | 7.1 | 20.2 | — | 17.8 | 19.4 | 21.4 | 14.2 | 24.7 | — |
| Wt %/Hour | — | — | — | — | — | — | — | — | — | — | — |
| Reaction Condition | | | | | | | | | | | |
| Temperature, °C. | 244 | 243 | 242 | 243 | 234 | 234 | 226 | 235 | 248 | 201 | 196 |
| HSi(OMe)$_3$/Si(MeO)$_4$ Ratio | 0.001 | — | 0.13 | 0.001 | 0.53 | — | — | — | — | — | — |

Charge - Si - 50.0 grams Active Mass (PHP) (**added 25 grams Li)
Catalyst - 5 grams Cuprous Chloride
Solvent - 101 grams THERMINOL ®
101 grams KEMAMINE ® (50%)

| | | | | | | | | | | |
|---|---|---|---|---|---|---|---|---|---|---|
| Sample Collected, Grams | 38.3 | 57.0 | * | 72.8 | * | 40.4 | 74.2 | 66.3 | * | 61.4 |
| Reaction Time, Minutes | 120 | 120 | * | 120 | * | 75 | 120 | 120 | * | 120 |
| MeOH Feed, Grams | 33.2 | 53.0 | * | 67.3 | * | 30.9 | 60.9 | 60.9 | * | 56.2 |
| GCA | | | | | | | | | | |
| MeOH | 89.7 | 48.6 | 48.5 | 50.6 | 43.3 | 47.4 | 51.6 | 72.5 | 88.7 | 93.1 |
| HSi(OMe)$_3$ | — | — | — | — | 3.2 | — | — | — | — | — |
| Si(MeO)$_4$ | 4.8 | 44.6 | 43.3 | 40.0 | 47.7 | 43.8 | 38.7 | 20.1 | 1.4 | 0.5 |
| Others (Si) | 0.1 | 0.4 | 0.5 | 0.3 | 0.4 | 0.4 | 0.3 | 0.1 | 0.03 | — |
| Solvent | 5.4 | 6.4 | 7.7 | 9.1 | 5.4 | 8.4 | 9.4 | 7.3 | 9.9 | 6.4 |
| Si Conversion | 11.1 | 35.75** | — | 31.0 | — | 25.6 | 22.3 | 17.0 | — | 14.5 |
| (Si in Pot grams) | | | | | | | | | | |
| Total Si in Sample | 0.347 | 4.735 | — | 5.414 | — | 3.297 | 5.341 | 2.470 | — | 0.057 |
| gms/hour | 0.17 | 2.37 | — | 2.71 | — | 2.64 | 2.67 | 1.23 | — | 0.028 |
| wt %/hour | 1.57 | 6.67 | — | 8.73 | — | 10.3 | 12.0 | 7.26 | — | 0.19 |
| MeOH Conversion | | | | | | | | | | |
| Feed Rate gms/hour | 16.6 | 26.5 | — | 33.6 | — | 24.7 | 30.5 | 30.5 | — | 28.1 |
| Wt %/Hour | — | — | — | — | — | — | — | — | — | — |
| Reaction Condition | | | | | | | | | | |
| Temperature, °C. | 247 | 247 | 253 | 253 | 255 | 260 | 253 | 252 | 256 | 243 |
| HSi(OMe)$_3$/Si(MeO)$_4$ Ratio | — | — | — | — | 0.067 | — | — | — | — | — |

*Instantaneous Sample

TABLE 7

Charge - Si - 50.0 grams Active Mass
Catalyst - 5 grams Cuprous Chloride
Solvent - 50/50 MTG to THERMINOL ® 60

| | | | | | | | | | | | |
|---|---|---|---|---|---|---|---|---|---|---|---|
| Sample Collected, Grams | 50.7 | 45.1 | 28.1 | 49.2 | 51.5 | 50.0 | 48.0 | 44.9 | 20.9 | 43.1 | 20.4 |
| Reaction Time, Minutes | 148 | 76 | 92 | 79 | 84 | 60 | 72 | 77 | 62 | 191 | 63 |
| MeOH Feed, Grams | 73.0 | 41.15 | 23.74 | 48.28 | 47.49 | 45.11 | 35.6 | 33.24 | 18.2 | 29.28 | 26.11 |
| GCA | | | | | | | | | | | |
| MeOH | 31.08 | 38.22 | 40.48 | 40.43 | 36.76 | 26.12 | 59.8 | 77.69 | 87.52 | 85.05 | 91.03 |
| HSi(OMe)$_3$ | 6.39 | 15.51 | 12.09 | 13.35 | 12.52 | 9.84 | 0.86 | — | — | — | — |
| Si(MeO)$_4$ | 54.16 | 40.75 | 41.30 | 41.90 | 46.75 | 48.16 | 33.63 | 15.37 | 9.33 | 5.19 | 4.01 |
| Others (Si) | 2.77 | 1.64 | 1.24 | 1.21 | 1.08 | 0.67 | 0.27 | 0.28 | 0.24 | 0.40 | 0.16 |
| Solvent | 5.60 | 3.91 | 4.90 | 3.11 | 2.89 | 5.21 | 5.41 | 6.67 | 1.94 | 9.32 | 4.81 |
| Si Conversion | 50.0 | 43.88 | 38.72 | 35.72 | 29.33 | 23.29 | 17.65 | 14.55 | 13.25 | 12.88 | 12.42 |
| (Si in Pot grams) | | | | | | | | | | | |
| Total Si in Sample | 6.12 | 5.16 | 3.00 | 6.39 | 6.04 | 5.64 | 3.10 | 1.30 | 0.37 | 0.46 | 0.16 |
| gms/hour | 2.48 | 4.07 | 1.95 | 4.85 | 4.32 | 5.64 | 2.58 | 1.01 | 0.37 | 0.14 | 0.15 |
| wt %/hour | 4.97 | 9.29 | 5.05 | 13.58 | 14.72 | 24.22 | 14.63 | 6.96 | 2.80 | 1.11 | 1.21 |
| MeOH Conversion | | | | | | | | | | | |
| Feed Rate gms/hour | 29.6 | 32.5 | 15.5 | 36.7 | 33.9 | 45.1 | 29.7 | 29.9 | 17.6 | 9.2 | 24.9 |
| Wt %/Hour | — | — | — | — | — | — | — | — | — | — | — |
| Reaction Condition | | | | | | | | | | | |
| Temperature, °C. | 240 | 240 | 242 | 240 | 243 | 240 | 244 | 240 | 232 | 230 | 241 |
| HSi(OMe)$_3$/Si(MeO)$_4$ Ratio | 0.118 | 0.381 | 0.293 | 0.319 | 0.268 | 0.204 | 0.026 | — | — | — | — |
| Sample Collected, Grams | 41.1 | 47.7 | 46.3 | 42.0 | 45.9 | 48.5 | 41.8 | 42.7 | 44.1 | 37.1 | |
| Reaction Time, Minutes | 135 | 55 | 85 | 79 | 91 | 72 | 92 | 124 | 84 | 70 | |
| MeOH Feed, Grams | 235.61 | 31.66 | 43.53 | 35.61 | 38.78 | 34.99 | 37.2 | 38.91 | 34.82 | 34.03 | |
| GCA | | | | | | | | | | | |

TABLE 7-continued

Charge - Si - 50.0 grams Active Mass
Catalyst - 5 grams Cuprous Chloride
Solvent - 50/50 MTG to THERMINOL ® 60

| | | | | | | | | | | |
|---|---|---|---|---|---|---|---|---|---|---|
| MeOH | 88.81 | 82.90 | 86.52 | 88.37 | 88.31 | 85.61 | 89.79 | 92.69 | 87.44 | 91.65 |
| HSi(OMe)$_3$ | — | — | — | — | — | — | — | 0.03 | 0.01 | 0.04 |
| Si(MeO)$_4$ | 2.86 | 2.64 | 2.34 | 1.85 | 1.68 | 1.62 | 1.48 | 0.88 | 0.67 | 0.60 |
| Others (Si) | 0.35 | 0.94 | 0.69 | 0.68 | 0.54 | 0.73 | 0.47 | 0.58 | 1.02 | 0.89 |
| Solvent | 7.98 | 13.52 | 10.41 | 9.10 | 9.49 | 12.03 | 13.32 | 5.82 | 10.85 | 6.87 |
| Si Conversion | 62.26 | 62.01 | 61.67 | 61.40 | 61.69 | 60.99 | 60.76 | 60.60 | 60.47 | 60.31 |
| (Si in Pot grams) | | | | | | | | | | |
| Total Si in Sample | 0.25 | 0.34 | 0.27 | 0.21 | 0.20 | 0.23 | 0.16 | 0.13 | 0.16 | 0.12 |
| gms/hour | 0.11 | 0.37 | 0.19 | 0.16 | 0.13 | 0.19 | 0.10 | 0.06 | 0.11 | 0.10 |
| wt %/hour | 0.18 | 0.59 | 0.31 | 0.26 | 0.21 | 0.31 | 0.17 | 0.10 | 0.19 | 0.17 |
| MeOH Conversion | | | | | | | | | | |
| Feed Rate gms/hour | 15.8 | 34.5 | 30.7 | 27.0 | 25.6 | 29.2 | 34.3 | 18.8 | 24.9 | 29.2 |
| Wt %/Hour | — | — | — | — | — | — | — | — | — | — |
| Reaction Condition | | | | | | | | | | |
| Temperature, °C. | 242 | 242 | 245 | 240 | 241 | 241 | 240 | 244 | 238 | 242 |
| HSi(OMe)$_3$/Si(MeO)$_4$ Ratio | — | — | — | — | 0.067 | — | — | — | — | — |

*50 grams of Silicon Metal added to reaction before starting to heat up (65 to 150 mesh) Not Activated

TABLE 8

Charge: - Si - 50.0 grams Active Mass (PHP)
Catalyst - 5 grams Dry Cuprous Cl
Solvent - 150 grams THERMINOL ®
50 grams KEMAMINE ® 25%
Used 5 Plated Oldershaw Column

| | | | | | | | | | | | | | | | |
|---|---|---|---|---|---|---|---|---|---|---|---|---|---|---|---|
| Sample Collected, Grams | 47.8 | 29.8 | 50.5 | * | 51.9 | 28.0 | 13.5 | * | 27.1 | 24.4 | 46.5 | * | 36.8 | 82.0 | 33.4 |
| Reaction Time, Minutes | 240 | 130 | 120 | * | 120 | 90 | 120 | * | 120 | 60 | 120 | * | 120 | 90 | 60 |
| MeOH Feed, Grams | 67.3 | 31.7 | 49.1 | * | 57.8 | 27.7 | 19.8 | * | 27.7 | 23.7 | 45.1 | * | 37.2 | 75.2 | 31.7 |
| GCA | | | | | | | | | | | | | | | |
| MeOH | 62.0 | 62.9 | 56.7 | 71.1 | 62.0 | 53.5 | 50.3 | 46.4 | 41.5 | 49.9 | 61.2 | 63.1 | 59.6 | 69.5 | 62.7 |
| HSi(OMe)$_3$ | 0.1 | 0.1 | — | 3.9 | — | 0.03 | 0.03 | 3.1 | 0.02 | 0.02 | 0.05 | 4.0 | 0.05 | — | — |
| Si(MeO)$_4$ | 36.1 | 32.9 | 42.3 | 24.2 | 37.2 | 44.3 | 46.9 | 47.4 | 55.8 | 44.5 | 33.8 | 29.2 | 36.0 | 21.1 | 31.6 |
| Others (Si) | 1.8 | 4.1 | 1.0 | 0.8 | 0.8 | 1.1 | 1.8 | 1.5 | 1.3 | 1.0 | 1.5 | 1.7 | 1.6 | 0.5 | 0.7 |
| Solvent** | — | — | — | — | — | 1.1 | 1.0 | 1.6 | 1.4 | 4.6 | 3.4 | 2.0 | 2.7 | 8.9 | 5.0 |
| Si Conversion | 50.0 | 46.6 | 44.5 | — | 60.4 | 36.7 | 34.3 | — | 33.1 | 30.2 | 28.2 | — | 25.1 | 22.5 | 19.2 |
| (Si in Pot grams) | | | | | | | | | | | | | | | |
| Total Si in Sample | 3.387 | 2.094 | 4.051 | — | 3.652 | 2.358 | 1.223 | — | 2.868 | 2.057 | 3.061 | — | 2.58 | 3.281 | 2.00 |
| gms/hour | 0.85 | 0.96 | 2.03 | — | 1.83 | 1.57 | 0.61 | — | 1.43 | 2.06 | 1.53 | — | 1.29 | 2.19 | 2.00 |
| wt %/hour | 1.69 | 2.07 | 4.55 | — | 4.52 | 4.28 | 1.78 | — | 4.33 | 6.81 | 5.43 | — | 5.14 | 9.27 | 10.41 |
| MeOH Conversion | | | | | | | | | | | | | | | |
| Feed Rate gms/hour | 16.8 | 14.6 | 24.6 | — | 28.9 | 18.5 | 9.9 | — | 13.8 | 23.7 | 22.6 | — | 18.6 | 50.1 | 31.7 |
| Wt %/hour | — | — | — | — | — | — | — | — | — | — | — | — | — | — | — |
| Reaction Condition | | | | | | | | | | | | | | | |
| Temperature, °C. | 225 | 254 | 239 | 240 | 252 | 254 | 251 | 248 | 249 | 251 | 260 | 261 | 261 | 253 | 260 |

*Instantaneous Sample
**Includes Heavies

TABLE 9

Charge - Si - 50.0 grams Active Mass (PHP)
Catalyst - 5 grams Cuprous Chloride
Solvent - 190 grams THERMINOL ®
10 grams KEMAMINE ® (5%)

| | | | | | | | | | | |
|---|---|---|---|---|---|---|---|---|---|---|
| Sample Collected, Grams | 67.6 | * | 80.0 | 71.5 | * | 62.1 | 70.0 | * | 43.2 | 50.9 |
| Reaction Time, Minutes | 120 | * | 105 | 90 | * | 120 | 120 | * | 60 | 60 |
| MeOH Feed, Grams | 63.3 | * | 70.4 | 64.1 | * | 61.7 | 68.1 | * | 41.9 | 49.9 |
| GCA | | | | | | | | | | |
| MeOH | 41.1 | 28.7 | 52.6 | 58.6 | 49.3 | 44.0 | 43.2 | 51.5 | 42.2 | 40.9 |
| HSi(OMe)$_3$ | 17.5 | 13.4 | 0.04 | — | 31.7 | 1.9 | — | 13.4 | 0.1 | 0.6 |
| Si(MeO)$_4$ | 32.5 | 52.6 | 35.2 | 31.5 | 15.1 | 49.9 | 49.5 | 24.2 | 53.1 | 53.6 |
| Others (Si) | 2.0 | 1.9 | 0.6 | 0.8 | 1.3 | 1.4 | 0.9 | 1.3 | 0.5 | 0.4 |
| Solvent** | 6.9 | 3.4 | 11.6 | 9.1 | 2.6 | 2.8 | 6.4 | 9.6 | 4.1 | 4.5 |
| Si Conversion | 50.0 | — | 42.9 | 37.6 | — | 33.3 | 27.1 | — | 20.6 | 16.3 |
| (Si in Pot grams) | | | | | | | | | | |
| Total Si in Sample | 7.073 | — | 5.305 | 4.280 | — | 6.179 | 6.527 | — | 4.286 | 5.142 |
| gms/hour | 3.54 | — | 3.03 | 2.85 | — | 3.09 | 3.26 | — | 4.29 | 5.14 |
| wt %/hour | 7.07 | — | 7.07 | 7.59 | — | 9.28 | 12.0 | — | 20.8 | 31.5 |
| MeOH Conversion | | | | | | | | | | |
| Feed Rate gms/hour | 31.7 | — | 48.6 | 42.7 | — | 30.85 | 34.0 | — | 41.9 | 49.9 |
| Wt %/hour | — | — | — | — | — | — | — | — | — | — |
| Reaction Condition | | | | | | | | | | |
| Temperature, °C. | 255 | 248 | 251 | 255 | 256 | 255 | 255 | 253 | 253 | 252 |

TABLE 9-continued

Charge - Si - 50.0 grams Active Mass (PHP)
Catalyst - 5 grams Cuprous Chloride
Solvent - 190 grams THERMINOL ®
10 grams KEMANINE ® (5%)

| HSi(OMe)$_3$/Si(MeO)$_4$ Ratio | 0.54 | 0.25 | — | — | 2.10 | 0.04 | — | 0.55 | 0.002 | 0.01 |
|---|---|---|---|---|---|---|---|---|---|---|

*Instantaneous Sample
**Includes Heavies

TABLE 10

Silicon Charge - 50.0 Gms 95/150 Production Grade
Catalyst - 0.33 Gms of CuII(OH) Dried Old Std.
Solvent - 98.0 Gms of THERMINOL ®-60
2.0 Gms. KEMAMINE ®T-9742D

| SAMPLE TAKEN (GM) | RX TIME (MIN) | METHANOL FEED (GM) | METHANOL RATE (GM/H) | GC ANALYSIS (%) MEOH | TRI | TETR | SIOSI | SOL | Si IN POT (GM) | Si/SAMPLE TOTAL (GM) | Si/SAMPLE RATE (GM/H) | RATIO SAMP | RATIO ACCU |
|---|---|---|---|---|---|---|---|---|---|---|---|---|---|
| 34.7 | 60 | 41.2 | 41.2 | 46.3 | 26.5 | 25.2 | 1.1 | 0.8 | 50.00 | 3.81 | 3.8 | 1.1 | 1.1 |
| 45.3 | 63 | 41.9 | 39.9 | 28.9 | 56.9 | 13.5 | 0.7 | 0.0 | 46.19 | 7.11 | 6.8 | 4.2 | 2.4 |
| 47.9 | 68 | 43.5 | 38.4 | 37.8 | 48.9 | 12.7 | 0.7 | 0.0 | 39.08 | 6.57 | 5.8 | 3.9 | 2.8 |
| 45.6 | 66 | 47.5 | 43.2 | 50.1 | 36.9 | 12.4 | 0.7 | 0.0 | 32.50 | 4.98 | 4.5 | 3.0 | 2.8 |
| 43.7 | 60 | 43.5 | 43.5 | 60.1 | 27.8 | 11.5 | 0.5 | 0.1 | 27.53 | 3.76 | 3.8 | 2.4 | 2.8 |
| 55.3 | 86 | 53.8 | 37.5 | 67.7 | 17.6 | 14.0 | 0.4 | 0.2 | 23.76 | 3.71 | 2.6 | 1.3 | 2.5 |
| 41.9 | 60 | 39.6 | 39.6 | 63.6 | 13.0 | 22.6 | 0.8 | 0.0 | 20.05 | 3.07 | 3.1 | 0.6 | 2.1 |
| 48.5 | 69 | 47.5 | 41.3 | 75.4 | 10.6 | 13.1 | 0.8 | 0.1 | 16.98 | 2.44 | 2.1 | 0.8 | 2.0 |
| 46.9 | 68 | 47.5 | 41.9 | 83.1 | 5.6 | 10.1 | 0.7 | 0.4 | 14.54 | 1.55 | 1.4 | 0.6 | 1.8 |
| 40.3 | 60 | 37.2 | 37.2 | 86.8 | 4.7 | 7.7 | 0.6 | 0.1 | 12.99 | 1.06 | 1.1 | 0.6 | 1.8 |
| 41.6 | 60 | 41.9 | 41.9 | 86.7 | 0.1 | 10.7 | 0.7 | 1.8 | 11.93 | 0.90 | 0.9 | 0.0 | 1.7 |
| 48.1 | 70 | 47.5 | 40.7 | 88.2 | 0.1 | 9.0 | 0.6 | 2.2 | 11.03 | 0.87 | 0.7 | 0.0 | 1.6 |
| 53.7 | 80 | 51.4 | 38.6 | 89.9 | 0.1 | 7.3 | 0.5 | 2.3 | 10.16 | 0.80 | 0.6 | 0.0 | 1.5 |
| 48.5 | 62 | 43.5 | 42.1 | 84.7 | 2.6 | 9.4 | 0.5 | 2.7 | 9.36 | 1.18 | 1.1 | 0.3 | 1.4 |
| 85.2 | 122 | 83.1 | 40.9 | 90.6 | 0.7 | 4.8 | 0.4 | 4.1 | 8.18 | 0.97 | 0.5 | 0.1 | 1.4 |
| 90.3 | 131 | 87.1 | 39.9 | 93.0 | 0.6 | 2.3 | 0.3 | 3.8 | 7.21 | 0.57 | 0.3 | 0.3 | 1.3 |
| 83.9 | 120 | 83.1 | 41.6 | 91.9 | 0.0 | 3.8 | 0.3 | 4.0 | 6.64 | 0.65 | 0.3 | 0.0 | 1.3 |

The mole percent trimethoxysilane produced is 52.6733
The mole percent tetramethoxysilane produced is 33.02583

TABLE 11

Silicon Charge - 50.0 Gms 95/150 Production Grade
Catalyst - 0.33 Gms of CuII(OH) Stabilized Old Std.
Solvent - 100.0 Gms of THERMINOL ®-60
2.0 Gms. KEMAMINE ®

| SAMPLE TAKEN (GM) | RX TIME (MIN) | METHANOL FEED (GM) | METHANOL RATE (GM/H) | GC ANALYSIS (%) MEOH | TRI | TETR | SIOSI | SOL | Si IN POT (GM) | Si/SAMPLE TOTAL (GM) | Si/SAMPLE RATE (GM/H) | RATIO SAMP | RATIO ACCU |
|---|---|---|---|---|---|---|---|---|---|---|---|---|---|
| 78.8 | 117 | 79.1 | 40.6 | 95.7 | 0.0 | 0.2 | 0.0 | 4.1 | 50.00 | 0.03 | 0.0 | 0.0 | 0.0 |
| 100.2 | 141 | 98.9 | 42.1 | 95.6 | 0.0 | 0.0 | 0.0 | 4.3 | 49.97 | 0.01 | 0.0 | 0.0 | 0.0 |
| 84.0 | 123 | 79.1 | 38.6 | 95.4 | 0.0 | 0.0 | 0.0 | 4.6 | 49.96 | 0.00 | 0.0 | 0.0 | 0.0 |
| 56.4 | 86 | 55.4 | 38.7 | 95.8 | 0.0 | 0.0 | 0.0 | 4.1 | 49.96 | 0.00 | 0.0 | 0.0 | 0.0 |
| 84.3 | 120 | 81.5 | 40.8 | 95.2 | 0.0 | 0.0 | 0.0 | 4.8 | 49.95 | 0.01 | 0.0 | 0.0 | 0.0 |
| 103.2 | 147 | 100.5 | 41.0 | 95.7 | 0.0 | 0.0 | 0.0 | 4.3 | 49.95 | 0.00 | 0.0 | 1.0 | 0.0 |
| 83.7 | 123 | 80.7 | 39.4 | 96.0 | 0.0 | 0.0 | 0.0 | 4.0 | 49.95 | 0.00 | 0.0 | 1.0 | 0.0 |
| 49.2 | 75 | 49.9 | 39.9 | 96.7 | 0.0 | 0.0 | 0.0 | 3.3 | 49.95 | 0.00 | 0.0 | 1.0 | 0.0 |
| 27.8 | 60 | 31.7 | 31.7 | 63.3 | 5.6 | 27.7 | 1.8 | 1.6 | 49.95 | 1.89 | 1.9 | 0.2 | 0.2 |
| 43.5 | 59 | 39.6 | 40.3 | 31.0 | 50.6 | 17.5 | 0.8 | 0.1 | 48.06 | 6.53 | 6.6 | 2.9 | 1.5 |
| 90.8 | 128 | 87.1 | 40.8 | 46.9 | 36.7 | 15.5 | 0.8 | 0.2 | 41.52 | 10.41 | 4.9 | 2.4 | 1.9 |
| 82.7 | 120 | 83.1 | 41.6 | 69.2 | 16.7 | 12.7 | 0.9 | 0.4 | 31.12 | 5.28 | 2.6 | 1.3 | 1.8 |
| 70.8 | 108 | 68.9 | 38.3 | 78.2 | 8.7 | 11.8 | 0.6 | 0.6 | 25.84 | 3.05 | 1.7 | 0.7 | 1.6· |
| 85.1 | 120 | 80.7 | 40.3 | 71.7 | 1.5 | 24.2 | 1.3 | 1.3 | 22.79 | 4.34 | 2.2 | 0.1 | 1.1 |
| 98.6 | 140 | 95.8 | 41.1 | 81.3 | 0.2 | 15.5 | 0.8 | 2.2 | 18.45 | 3.04 | 1.3 | 0.0 | 0.9 |
| 86.2 | 127 | 84.7 | 40.0 | 84.0 | 0.3 | 12.4 | 0.6 | 2.8 | 15.41 | 2.15 | 1.0 | 0.0 | 0.8 |
| 56.9 | 85 | 55.4 | 39.1 | 87.1 | 1.8 | 8.4 | 0.6 | 2.1 | 13.26 | 1.19 | 0.8 | 0.2 | 0.8 |

The mole percent trimethoxysilane is 36.54631
The mole percent tetramethoxysilane produced in 36.7938

That which is claimed is:

1. A process for producing controlled trialkoxysilane/tetraalkoxysilane mixtures of the formula HSi(OR)$_3$/Si(OR)$_4$ wherein R is an alkyl group containing from 1 to 6 carbon atoms which comprises:
   (a) forming a reaction mixture comprising an alcohol of the formula ROH wherein R is as defined above, a mixed solvent, silicon metal, and a catalytically effective amount of copper catalyst; and
   (b) reacting said alcohol with said silicon metal in the presence of said copper catalyst and mixed solvent to produce the trialkoxysilane/tetraalkoxysilane mixture,
   wherein said mixed solvent comprises a first, inert solvent that does not degrade during the reaction and a second solvent which is a Lewis base that acts to promote the reaction between trialkoxysilanes and alcohol.

2. The process of claim 1 wherein R is methyl.

3. The process of claim 1 wherein the first, inert solvent is an organic solvent.

4. The process of claim 3 wherein the first, inert solvent is a heat transfer fluid.

5. The process of claim 3 wherein the first, inert solvent is dodecyclobenzene.

6. The process of claim 1 wherein the second solvent has a pKa greater than 7.

7. The process of claim 6 wherein the second solvent is selected from the group of tertiary amines, polyethers and aromatic ethers.

8. The process of claim 7 wherein the second solvent is methoxytriglycol.

9. The process of claim 7 wherein the second solvent is diphenyl oxide.

10. The process of claim 1 wherein the copper catalyst is a stabilized copper (II) hydroxide.

11. The process of claim 1 wherein R is ethyl.

* * * * *